(12) United States Patent  
Mathews

(10) Patent No.: US 7,407,629 B2  
(45) Date of Patent: Aug. 5, 2008

(54) SPECIMEN ORIENTATION TAGS AND DISPENSER

(76) Inventor: John Mathews, 490 Flats Rd., Athens, NY (US) 12015

( * ) Notice: Subject to any disclaimer, the term of this patent is extended or adjusted under 35 U.S.C. 154(b) by 657 days.

(21) Appl. No.: 11/068,542

(22) Filed: Feb. 28, 2005

(65) Prior Publication Data

US 2006/0191951 A1   Aug. 31, 2006

(51) Int. Cl.
*B23Q 7/04* (2006.01)
(52) U.S. Cl. .................. 422/102; 378/163; 221/210
(58) Field of Classification Search ............... 422/102; 221/5; 606/151; 378/163
See application file for complete search history.

(56) References Cited

U.S. PATENT DOCUMENTS

| 5,000,484 | A |   | 3/1991  | Phelan et al. |
| 5,474,569 | A | * | 12/1995 | Zinreich et al. ............. 606/151 |
| 5,524,634 | A |   | 6/1996  | Turkel et al. |
| 5,664,697 | A | * | 9/1997  | Lambelet et al. ............. 221/5 |
| 5,817,032 | A |   | 10/1998 | Williamson, IV et al. |
| 6,225,107 | B1 |  | 5/2001  | Nagle |
| 6,432,064 | B1 |  | 8/2002  | Hibner et al. |
| 6,605,047 | B2 |  | 8/2003  | Zarins et al. |
| 6,752,154 | B2 |  | 6/2004  | Fogarty et al. |
| 2004/0052333 | A1 | * | 3/2004 | Sayre et al. ............. 378/163 |

OTHER PUBLICATIONS

U.S. Appl. No. 10/243,352, filed Sep. 13, 2002.

* cited by examiner

*Primary Examiner*—Walter D. Griffin
*Assistant Examiner*—Christine T Mui
(74) *Attorney, Agent, or Firm*—Sander Rabin

(57) ABSTRACT

The present invention comprises a device for anatomically orienting at least one tissue specimen, comprising a dispenser for carrying and selectably dispensing at least one pre-labeled specimen orientation tag. The dispenser comprises a vessel separable along its equator into an inferior base segment and a superior cover segment. The inferior base segment and superior cover segment enclose a dispensing ring that includes at least one set of paired radially projecting retaining prongs, which paired prongs define at least one dispensing bay, in which the specimen orientation tag is disposed for selective dispensation through at least one aperture radially arrayed along the equator of the dispsenser.

14 Claims, 4 Drawing Sheets

SPECIMEN ORIENTATION TAGS AND DISPENSER

BACKGROUND OF THE INVENTION

1. Technical Field

The present invention relates to pathologic evaluation of tissue specimens and in particular to the identification of the anatomic orientation of tissue specimens submitted for pathologic evaluation.

2. Related Art

Tissue specimens removed during surgery must be anatomically oriented with respect to structures from which they have been excised and the body of the patient in order for pathologists to make a proper pathological diagnoses.

By medical consensus and convention, anatomic orientation is made with respect to a standard anatomic position in which a human being stands erect with his or her arms supinated. With respect to the standard anatomic position, the head is superior or cephalad and the feet are inferior or caudad. The chest is anterior or ventral and the back is posterior or dorsal. The arms are lateral and the heart is medial.

In keeping with this convention, if for example, a tissue specimen is removed from the lobe of a patient's lung in the approximate form of a cube, the faces of the cube may be identified as: superior or cephalad; inferior or caudad; anterior or ventral; posterior or dorsal; lateral; and, medial.

Should the exemplary cube of tissue be found by a pathologist to contain a tumor, the orientation of the tumor with respect to the lung from which it has been removed will be critical to the surgical treatment of the patient. Accordingly, surgeons removing tissue specimens for pathological and histopathological diagnoses, and excising tissues until they are assured by a pathologist of tumor-free resection margins, must label the tissue specimens in a manner that unambiguously orients them with respect to the anatomical structure and person from which they are excised.

Such labeling is typically accomplished by passing a suture through as many faces or aspects of a tissue specimen as are required to orient it unambiguously. For example, a surgeon may place a short black silk suture along a medial aspect of a tissue specimen, and a long black silk suture along an inferior aspect of a tissue specimen. Alternatively, a surgeon may identify a lateral aspect of a tissue specimen by passing a double loop of suture through its lateral margin, and may identify an inferior margin by passing a single loop of suture through its inferior margin. Margins, aspects, or faces of a tissue specimen may also be distinguished and identified with respect to anatomical orientation by passing sutures of different colors.

In each case, the suture length, suture configuration (i.e., single loop, double loop, etc.) or suture color that establishes an anatomic orientation for a tissue specimen is dictated aloud to another health care provider in the operating room, such as, for example, a circulating nurse. The circulating nurse typically prepares a written legend that correlates each suture with the dictated anatomic orientation. The written legend accompanies tissue specimens to the pathology laboratory, where its anatomic orientating information is used in the pathologic evaluation of the tissue specimens. For example, after checking the orienting sutures against the legend, pathology laboratory personnel will know how each tissue specimen was originally seated prior to its removal. This information is essential to accurate pathologic descriptions of the specimen and its surrounding tissues.

Establishing the anatomic orientation of a tissue specimen by the use of sutures of different lengths, colors or configuration is confusing and prone to errors. For example, sutures may unravel and the foregoing legend may be transcribed improperly or may be poorly legible.

Accordingly, there exists a need for the efficient, convenient and unambiguous anatomic orientation of tissue specimens for purposes of pathological diagnoses, and pathologically-guided surgical resections.

SUMMARY OF THE INVENTION

The present invention comprises a device for anatomically orienting at least one tissue specimen, comprising a dispenser for carrying and selectably dispensing at least one pre-labeled specimen orientation tag. The dispenser comprises a vessel separable along its equator into an inferior base segment and a superior cover segment. The inferior base segment and superior cover segment enclose a dispensing ring that includes at least one set of paired radially projecting retaining prongs, each set of which defines at least one dispensing bay, in which the specimen orientation tag is disposed for selective dispensation through at least one aperture radially arrayed along the equator of the dispsenser.

DETAILED DESCRIPTION OF THE INVENTION

Figure 1:
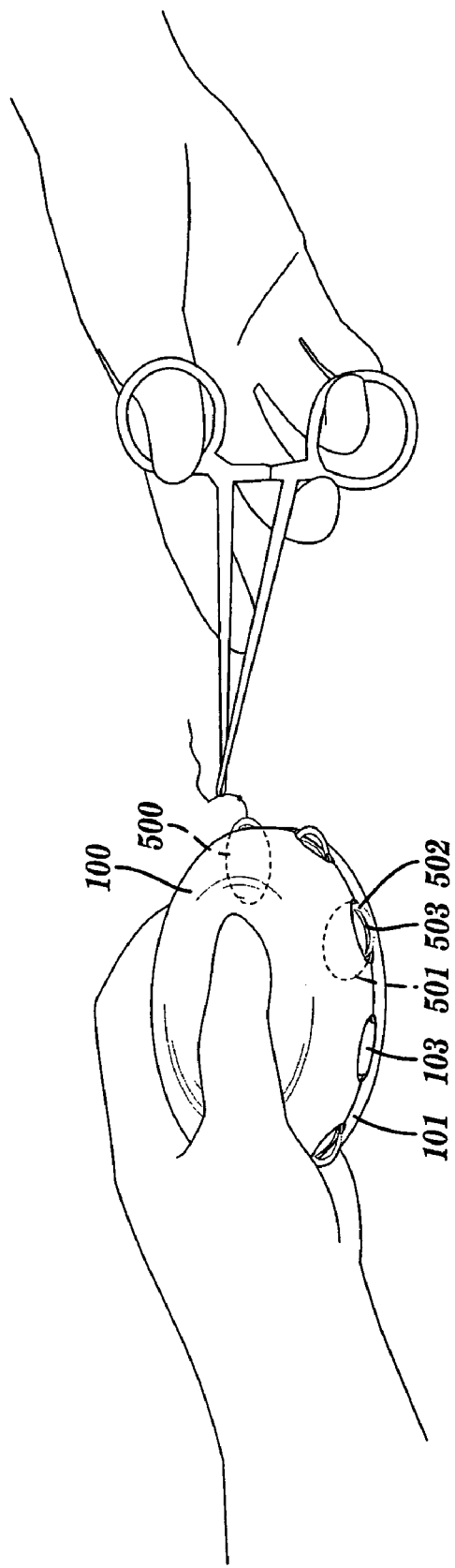
FIG. 1 is a schematic illustration of the invention held in the left hand of a surgeon as the surgeon uses his right hand to select and dispense a specimen orientation tag with a needle holder bearing a needle attached to a suture ligature.

FIG. 1 is a schematic illustration of the invention held in the left hand of a surgeon as the surgeon uses his right hand to select and dispense a specimen orientation tag with a needle holder bearing a needle attached to a suture ligature. As shown in FIG. 1, the invention comprises a plurality of specimen orientation tags 500 radially disposed within a dispenser 100 adapted to carry and dispense the specimen orientation tags 500. Each specimen orientation tag 500 has a body 501, from which a handle 502 extends through a plurality of apertures 103 that are radially arrayed along an equator 101 of dispenser 100. The body 501 and handle 502 of each specimen orientation tag 500 forms an eyelet 503 through which a suture ligature, surgical staple or other means for the attachment of the specimen orientation tag to a tissue specimen may be passed.

In an operating room or other surgical facility, the invention, manufactured as dispenser 100 preloaded with specimen orientation tags 500, is delivered, for example, by a circulating nurse, out of packaging that maintains the invention in a sterile state. Specimen orientation tags 500 and dispenser 100 are for single patient use only. Specimen orientation tags 500 are intended to orient tissue specimens for pathological evaluation and/or to label tissue specimens for anatomic orientation. Although biologically inert, specimen orientation tags 500 are not intended to remain in the patient.

The invention's packaging may be removed or peeled away by the circulating nurse and the sterilized invention is passed onto a sterile field by dropping it there or placing it within the reach of a scrub nurse or surgeon. The scrub nurse carefully verifies that the eyelet 503 of each specimen orientation tag 500, visibly protrudes through each aperture 103 that is radially arrayed along the equator of dispenser 100. As show in FIG. 1, the surgeon may grasp dispenser 100 in one hand and use a needle holder loaded with a suture ligature to grasp a specimen orientation tag 500 for fixation to an excised tissue specimen.

Specimen orientation tags 500 are dispensed one at a time by passing a suture needle through eyelet 503 of the desired specimen orientation tag 500 and then releasing it from a dispensing bay (not shown in FIG. 1) with a gentle tug. Each specimen orientation tag 500 is then secured to a tissue specimen with a surgical knot. When the tissue specimen is adequately tagged for orientation, it is passed out of the sterile surgical field to the circulating nurse.

The number of specimen orientation tags 500 remaining in dispenser 100 and the number of specimen orientation tags 500 that were dispensed should be included in the nurse's count sheet to verify that all specimen orientation tags 500 are accounted for prior to closure of the surgical wound.

Specimen Orientation Tags

Figure 2:
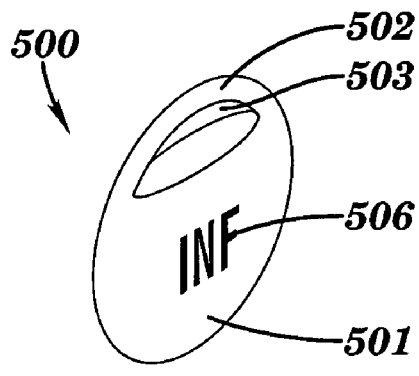
FIG. 2 is a perspective view of an exemplary specimen orientation tag bearing the exemplary inscription "INF."
Figure 3:
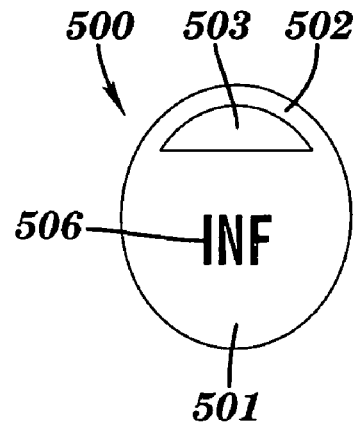
FIG. 3 is a front (elevated) view of an exemplary specimen orientation tag, as seen en face.
Figure 4:
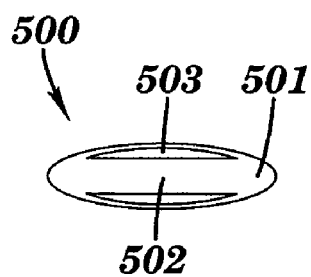
FIG. 4 is a top (plan) view of an exemplary specimen orientation tag, as seen on edge and from above.
Figure 5:
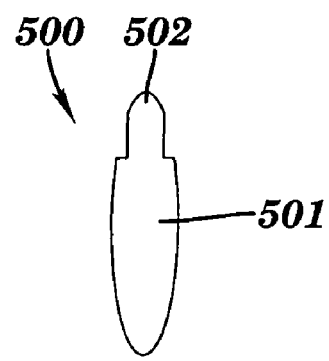
FIG. 5 is a lateral (elevated) view of an exemplary specimen orientation tag, as seen on edge and from the side.

FIGS. 2 through 5 are a series of illustrative views of an exemplary specimen orientation tag 500. FIG. 2 is a perspective view of an exemplary specimen orientation tag bearing the exemplary inscription 506 "INF." FIG. 3 is a front view of an exemplary specimen orientation tag, as seen en face. FIG. 4 is a top view of an exemplary specimen orientation tag, as seen on edge and from above. FIG. 5 is a lateral view of an exemplary specimen orientation tag, as seen on edge and from the side.

In FIGS. 2 through 5, an exemplary specimen orientation tag 500 is shown as having an exemplary elliptical shape. As shown in FIGS. 2 through 5, each specimen orientation tag 500 comprises a biologically inert and sterilizable body 501 and an eyelet 503, defined by a handle 502, through which a needle attached to a suture ligature (shown in FIG. 1) or surgical stapling device or other fixation or attachment means is passed to secure specimen orientation tag 500 to a tissue specimen.

Specimen orientation tag 500 may be made of a material such as, for example, polymethlymethacrylate, silicone, or any other biologically inert and sterilizable material. Specimen orientation tag 500 may have any shape. Specimen orientation tag 500 may additionally be made of a radio-opaque material to permit its identification on radiological images.

The exemplary elliptically-shaped specimen orientation tag 500 shown in FIGS. 2 through 5 may have a major diameter of about 1 cm and a minor diameter of about 0.75 cm. Body 501 may contribute about 0.75 cm to the major diameter, and handle 502 may contribute about 0.25 cm to the major diameter. The exemplary elliptically-shaped specimen orientation tag 500 shown in FIGS. 2 through 5 may have a thickness of about 0.25 cm.

Handle 502 of specimen orientation tag 500 may be extruded from body 501 or may be appended to body 501 by a suitable nontoxic, biologically inert adhesive, such as, for example, an acrylic-based glue. Eyelet 503 may alternatively be fashioned by drilling a hole into body 501.

Each face of body 501 of specimen orientation tag 500 bears an orientation designation, abbreviation, acronym or symbol 506 denoting an anatomical orientation. FIG. 2 and FIG. 3 show an exemplary specimen orientation tag 500 bearing the exemplary orientation acronym "INF," designating the word "inferior." Orientation designation, abbreviation, acronym or symbol 506 may be imprinted, engraved or otherwise affixed onto each face of body 501 of each specimen orientation tag 500.

The exemplary orientation acronyms appearing in Table 1 may be used as identifiers or anatomic orientation.

TABLE 1

| ORIENTATION ACRONYMS | |
|---|---|
| Anatomic Orientation | Abbreviation |
| Medial | MED |
| Lateral | LAT |
| Anterior | ANT |
| Ventral | VEN |
| Posterior | POS |
| Dorsal | DOR |
| Superior | SUP |
| Cephalad | CEP |
| Inferior | INF |
| Caudad | CAU |
| Left | LFT |
| Right | RGT |
| Area of Interest | AOI |

Specimen orientation tags 500 may be of like color or may be color-coded using any scheme that uniquely identifies each specimen orientation tag 500 with an anatomic orientation or the orientation acronym or symbol 506 that it bears.

Other labels may be created in lieu of an orientation designation, abbreviation, acronym or symbol for specific procedures having other labeling requirements. Moreover, such other labels may comprise designations, abbreviations, acronyms or symbols in foreign languages or icons that designate anatomic orientations.

As more fully described hereinafter, and as shown in FIG. 1, when specimen orientation tags 500 are arrayed for dispensation in dispenser 100, eyelets 503 are visibly accessible to easily enable a surgeon or scrub nurse to select a specimen orientation tag that is appropriate to label an excised tissue specimen. As shown in FIG. 1, once a specimen orientation tag 500 is "threaded," with a suture ligature, it is released from dispenser 100 with a tug on the suture. The suture carrying specimen orientation tag 500 is then secured to the tissue specimen by tying. Alternatively, specimen orientation tag 500 may be secured to a tissue specimen by means of a surgical stapling or other fastening device.

After placing the desired number of specimen orientation tags 500 to properly identify the anatomic orientation of a tissue specimen, the specimen is passed out of the surgical field to a circulating nurse and eventually delivered to a pathologist or other specialist for examination. Because specimen orientation tags 500 are placed by a surgeon (or scrub nurse) there is no need for a circulating nurse or other operating room assistant to create a separate written legend in order for a pathologist to orient the specimen.

Dispenser

Figure 6:
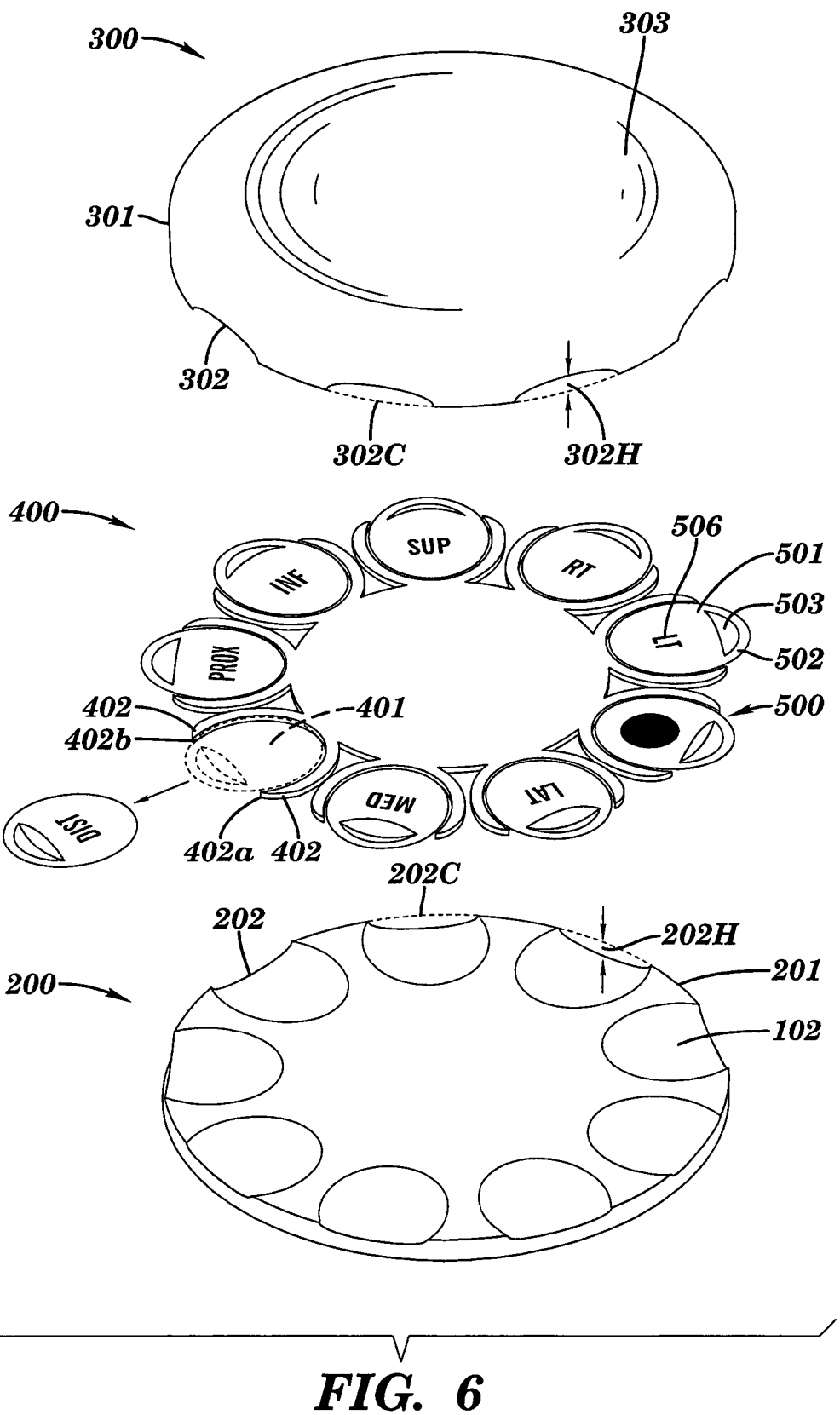
FIG. 6 is an exploded view of the invention, showing a cover segment superiorly and a base segment inferiorly, between which there is disposed a retaining ring with bays for the disposition of specimen orientation tags.
Figure 9:
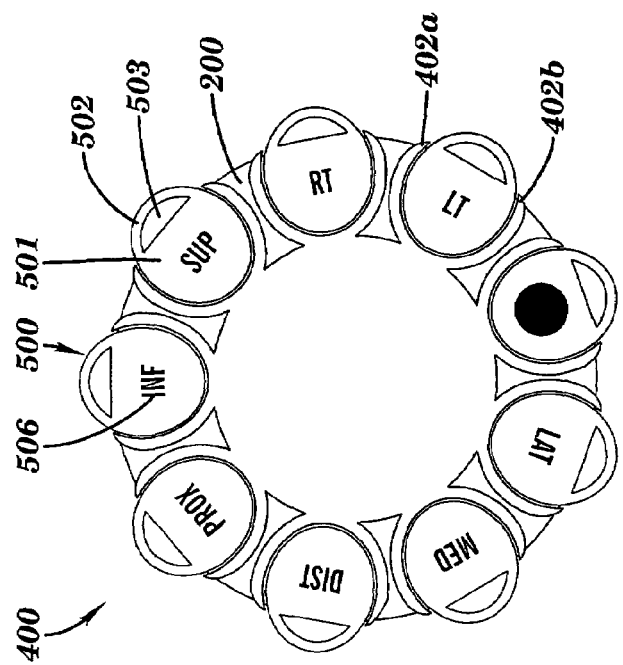
FIG. 9 is a top (plan) view of the dispenser's retaining ring seated in the base segment of the dispenser, as seen from above.
Figure 8:
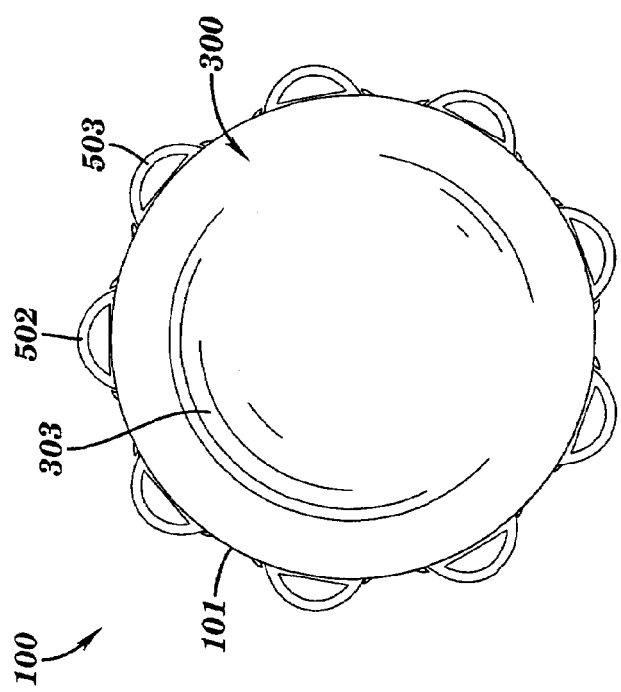
FIG. 8 is a top (plan) view of the dispenser, as seen from above.
Figure 7:
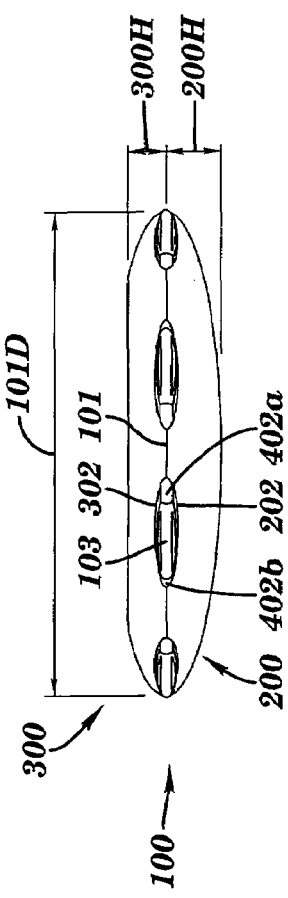
FIG. 7 is a lateral (elevated) view of the dispenser, as seen on edge and from the side.

FIGS. 6 through 9 are a series of illustrative views of exemplary dispenser 100 (FIG. 1) of specimen orientation tags 500. FIG. 6 is an exploded view of the invention, showing a cover segment superiorly and a base segment inferiorly, between which there is disposed a retaining ring with bays for the disposition of specimen orientation tags. FIG. 7 is a lateral view of the dispenser, as seen on edge and from the side. FIG. 8 is a top view of the dispenser, as seen from above. FIG. 9 is a top view of the dispenser's retaining ring seated in the base segment of the dispenser, as seen from above.

As shown in FIGS. 6 and 7, exemplary dispenser 100 for carrying and exemplary dispensing specimen orientation tags 500 comprises a vessel, in the exemplary form of a shallow oblate spheroid, separable along its equator 101 (FIG. 7) into an inferior base segment 200, in the form of a shallow inferior spherical cap, and an opposing superior cover segment 300, in the form of a shallow superior spherical cap. Base segment 200 and cover segment 300 enclose a dispensing ring 400 (FIG. 6).

Dispenser 100 and dispensing ring 400 may, for example, be made of sterilizable plastic, such as, for example, polymethylmethacrylate or silicone or any other biologically inert and sterilizable material.

As shown in FIG. 7, dispenser 100 may have a diameter 101D of about 5 cm. Cover segment 300, having the same diameter, may have a height 300H of about 0.5 cm. Base segment 200, having the same diameter, may also have a height 200H of about 0.5 cm. As shown in FIG. 6 and in FIG. 8, cover segment 300 includes a central concave depression 303 to facilitate grasping of dispenser 100 by the thumb of a user. Central concave depression 303 may have a diameter of about 3 cm and a depth of about 0.3 cm.

As shown in FIG. 6, a plurality of exemplary superior arcs 302 are fashioned into cover segment 300, so as to array them radially along equatorial perimeter 301 of cover segment 300. A plurality of exemplary inferior arcs 202 is fashioned into base segment 200, so as to array them radially along equatorial perimeter 201 of base segment 200. Exemplary superior arcs 302 and exemplary inferior arcs 202 appose one another when cover segment 300 is closed upon base segment 200. As shown in FIG. 7, the apposition of each superior arc 302 with its corresponding inferior arc 202 forms a plurality of exemplary elliptical apertures 103 along the equator 101 of dispenser 100. Perimeter 201 of base segment 200 and perimeter 301 of cover segment 300 are coincident with equator 101 of dispenser 100 when base segment 200 and cover segment 300 are apposed to form dispenser 100.

Each exemplary inferior arc 202, and each exemplary superior arc 302 may have equal corresponding chord lengths 202C, 302C of, for example, about 1 cm, and may have corresponding heights 202H, 302H of, for example, about 0.2 cm, thereby forming a generally elliptical aperture 103 (FIG. 7) with a major axis of about 1 cm and a minor axis of about 0.4 cm. Each exemplary elliptical aperture 103 provides access to a specimen orientation tag 500 disposed within a corresponding dispensing bay 401 of dispensing ring 400, more fully described hereinbelow in connection with FIG. 6 and FIG. 9.

As shown in FIG. 6 and FIG. 9, dispensing ring 400 includes a plurality of paired radially projecting retaining prongs 402 that oppose one another to secure specimen orientation tags 500. Each set of paired retaining prongs 402 defines a dispensing bay 401 (FIG. 6) having a diameter slightly smaller than a diameter of a specimen orientation tag, thereby permitting a user to easily release a specimen orientation tag from its dispensing bay 401. Each dispensing bay 401 corresponds to and is accessible through an exemplary elliptical aperture 103. Dispensing bays 401 are accordingly radially arrayed about retaining ring 400 to enable respective tips 402a and 402b of each pair of retaining prongs 402 protrude slightly from the opposing lateral margins of each exemplary elliptical aperture 103 in such a way as to retain specimen orientation tag 500 in dispensing bay 401 but not impede its removal.

As shown in FIG. 6, spoon-like indentations 102 are fashioned along the equatorial perimeter of base segment 200 to be coincident with dispensing bays 401 and exemplary elliptical apertures 103. Mirror-image spoon-like indentations (not shown in FIG. 6) are also fashioned along the equatorial perimeter of cover segment 300 to be coincident with dispensing bays 401 and exemplary elliptical apertures 103. When apposed, each spoon-like indentation 102 of base segment 200 forms a floor beneath its respective dispensing bay 401; and, each spoon-like indentation of cover segment 300 forms a roof over its respective dispensing bay.

When apposed, each spoon-like indentation 102 of base segment 200 and each corresponding spoon-like indentation of cover segment 300 creates a space in the general shape of an ellipsoid about each dispensing bay 401, that is accessible through its corresponding aperture 103. The spaces so formed, permit insertion of the tips of a surgical instrument, such as, for example, a needle holder or forceps, with which a specimen orientation tag may be grasped. Each spoon-like indentation may for example have a diameter of about 1 cm and a depth of about 0.2 cm.

If base segment 200 and cover segment 300 are made of a transparent material, the orientation designation, abbreviation, acronym or symbol 506 appearing on each specimen orientation tag will be visible through dispenser 100. If base segment 200 and cover segment 300 are made of a nontransparent material, then the inferior surface of base segment 200 and the superior surface of cover segment 300 are embossed or engraved with paired, radially arrayed If base segment 200 and cover segment 300 are made of a transparent material, the orientation designations, abbreviations, acronyms or symbols, each of which corresponds to the orientation If base segment 200 and cover segment 300 are made of a transparent material, the orientation designation, abbreviation, acronym or symbol of a proximal specimen orientation tag it overlies.

Dispenser 100 and specimen orientation tags 500 may be fabricated in various embodiments, in which the dimensions of dispenser 100 and specimen orientation tags 500 vary, and in which the number of specimen orientation tags 500 and their corresponding apertures 103, dispensing bays 401 and indentations 102 vary. For example a much smaller dispenser 100 may contain only a single specimen orientation tag, whereas, for example, a larger dispenser 100 may contain as many as twelve or more specimen orientation tags. This flexibility in features of the structure of the invention permits using specimen orientation tags that are appropriate to different specialized surgical procedures, such as, for example, a neurological biopsy or gynecological biopsy.

I claim:

1. An apparatus for anatomically orienting a plurality of tissue specimens, comprising a sterilizable dispenser for carrying and selectably dispensing a plurality of pre-labeled biologically inert, sterilizable, radio-opaque or radiolucent specimen orientation tags, said dispenser comprising a vessel separable along its equatorial perimeter into an inferior base segment and an opposing superior cover segment, which base segment and opposing cover segment enclose a sterilizable dispensing ring around which said a plurality of pre-labeled specimen orientation tag is disposed in a plurality of dispensing bays; said superior cover segment including a plurality of superior arcs along its equatorial perimeter and said inferior base segment including a plurality of corresponding inferior arcs along its equatorial perimeter, said superior and inferior arcs forming a plurality of generally elliptical apertures through which said specimen orientation tag is accessed.

2. The apparatus of claim 1, wherein said vessel comprises an oblate spheroid, said inferior base segment comprises an inferior spherical cap of said oblate spheroid and said superior cover segment comprises an opposing superior spherical cap of said oblate spheroid, which inferior spherical cap and opposing superior spherical cap close upon one another along an equator of said oblate spheroid.

3. The apparatus of claim 2, wherein said superior cover segment includes a central concave depression.

4. The apparatus of claim 1, wherein said superior cover segment includes a plurality of superior spoon-like indentations along its equatorial perimeter and said inferior base segment includes a plurality of corresponding inferior spoon-like indentations along its equatorial perimeter.

5. The apparatus of claim 4, wherein said a plurality of superior spoon-like indentations forms a roof above said a plurality of dispensing bays and said a plurality of corresponding inferior spoon-like indentations forms a corresponding floor beneath said a plurality of dispensing bays said at least one roof and said at least one corresponding floor forming a space about said a plurality of dispensing bays that is accessible through said at least one generally elliptical aperture along said equator of said oblate spheroid.

6. The apparatus of claim 1, wherein said dispensing ring includes a plurality of paired radially projecting retaining prongs that define said a plurality of dispensing bays, each dispensing bay having a diameter slightly smaller than a diameter of said a plurality of pre-labeled specimen orientation tags.

7. The apparatus of claim 6, wherein said a plurality of dispensing bays corresponds to and is accessible through said a plurality of generally elliptical apertures.

8. The apparatus of claim 1, wherein said a plurality of pre-labeled specimen orientation tags comprises a body and an eyelet.

9. The apparatus of claim 8, wherein said eyelet is defined by a handle appended to said body.

10. The apparatus of claim 8, wherein said eyelet is defined by an aperture in said body.

11. The apparatus of claim 8, wherein said eyelet provides means for the passage therethrough of a suture ligature.

12. The apparatus of claim 8, wherein said eyelet provides means for the passage therethrough of a surgical staple.

13. The apparatus of claim 8, wherein said eyelet provides means for the passage therethrough of any device for the attachment of said pre-labeled specimen orientation tag to a tissue specimen.

14. The apparatus of claim 8, wherein said a plurality of pre-labeled specimen orientation tags specimen orientation tag is color-coded in a scheme that uniquely identifies it with an anatomical orientation.

* * * * *